United States Patent [19]
Baum et al.

[11] Patent Number: 4,918,158
[45] Date of Patent: Apr. 17, 1990

[54] 1,3-DIETHYNYLADAMANTANE AND METHODS OF POLYMERIZATION THEREOF

[75] Inventors: Kurt Baum, Pasadena; Thomas G. Archibald, Los Angeles, both of Calif.

[73] Assignee: Fluorochem Inc., Azusa, Calif.

[21] Appl. No.: 887,219

[22] Filed: Jul. 21, 1986

[51] Int. Cl.$^4$ .............................................. C08F 1/26
[52] U.S. Cl. ........................................ 526/282; 585/21; 585/360
[58] Field of Search ................... 526/282; 585/21, 360

[56]         References Cited
        U.S. PATENT DOCUMENTS

| | | | |
|---|---|---|---|
| 3,342,880 | 9/1967 | Reinhardt | 526/282 |
| 3,382,288 | 5/1968 | Schneider | 585/360 |
| 3,518,241 | 6/1970 | Dolling et al. | 526/282 |
| 3,533,947 | 10/1970 | Dolling et al. | 526/282 |
| 3,639,362 | 2/1972 | Dolling et al. | 526/282 |
| 3,655,782 | 4/1972 | Moore | 585/21 |

FOREIGN PATENT DOCUMENTS 507592  5/1978  U.S.S.R. .............................. 526/282

Primary Examiner—Paul R. Michl
Assistant Examiner—Peter D. Mulcahy
Attorney, Agent, or Firm—John H. Crowe

[57]            ABSTRACT 1,3-Diethynyladamantane and a method of forming same by brominating adamantane to yield 1,3-dibromoadamantane, subjecting vinyl bromide to Friedel-Crafts alkylation with the 1,3-dibromoadamantane to form 1,3-bis(2,2-dibromoethyl)adamantane and subjecting the 1,3-bis(2,2-dibromoethyl)adamantane to dehydrohalogenation to yield the 1,3-diethynyladamantane. 1,3-Diethynyladamantane can be polymerized to produce strong, thermally stable resins suitable for advanced aerospace structural applications, as matrices for carbon-carbon systems and as electrical insulators. It can also be copolymerized with 1-ethynyladamantane to yield similarly useful resins.

14 Claims, No Drawings

1,3-DIETHYNYLADAMANTANE AND METHODS OF POLYMERIZATION THEREOF

The Government has rights in this invention pursuant to contract F33615-85-C-5139 awarded by the Department of the Air Force.

BACKGROUND OF THE INVENTION

This invention relates generally to 1,3-diethynyladamantane as a new composition of matter and to methods of synthesizing and polymerizing that compound into formulations having useful commercial properties. At present, composite matrix resins, structural adhesives and surface films are used for a number of aerospace structural applications. Presently available materials for such purposes lack adequate stability and suitable physical properties for certain system design applications. Also, there is a need for improved polymers for use as matrices for carbon-carbon systems. For such applications, polymers compatible with carbon fibers which can be pyrolyzed to yield dense, coherent matrices are needed. Another need is for thermally stable polymers with low dielectric constants for electrical insulator usage.

One approach heretofore taken to obtain improved thermally stable polymers for the above-indicated purposes has involved the attachment of acetylene groups to stable organic structures and polymerization of the acetylenic structures by cyclotrimerization or other mechanisms. Stable linking groups have thus been formed without the liberation of volatile by-products that would result in mechanical imperfections. Stable heterocycles, aromatic polyethers and similar materials have been linked in this manner. Still, there has existed a need for significant improvement in such materials for the above-indicated applications.

SUMMARY OF THE INVENTION

We have now, by this invention, succeeded in unexpectedly providing polymers of high thermal stability which are greatly superior to previously known polymeric systems for aerospace and other exotic purposes. We have accomplished this by providing a means of synthesizing 1,3-diethynyladamantane and polymerizing that compound to give a polymer of good thermooxidative stability and mechanical strength. Such properties are achieved through the incorporation of the adamantane nucleus, a highly stable organic structural unit, into the polymers. The 1,3-diethynyladamantane was a new diacetylene compound when we prepared it and, in addition to the polymerization of that compound, we have discovered that the diacetylene can be copolymerized with 1-ethynyladamantane to yield a strong, thermally stable resin.

We preceded our 1,3-diethynyladamantane work with a literature search, which revealed that only two mono-functional ethynyl-substituted adamantanes had been reported, these being 1-ethynyladamantane and 1,3,5,7-tetraethynyladamantane. See, Stetter H., Goebel, P. *Chem. Ber.* 1962 95, 1039 and Nakasaki, M.; Memura, K.; Hokura, Y. *J. Chem. Soc., Chem. Comm.* 1982, 1245, respectively. The literature search indicated that no attempts to polymerize those materials had been made. 1,3-Divinyladamantane has been recently reported, but 1,3-diethynyladamantane was unknown to us during our work in connection with that compound. The literature reference for the 1,3-divinyladamantane was Majerski, Z.; Skare, D.; Vulic, L. *Syn. Comm.* 1986 16 51. After our work had been completed, a publication appeared which described the synthesis of 1,3-diethynyladamantane by a procedure other than our procedure for producing that compound (Broxterman, Q. B.; Hogeveen, H.; Kingma, R. F. *Tetrahedron Letters* 1986, 27 1055). Several disubstituted acetylenes containing adamantane such as diadamantylacetylene and adamantylphenylacetylene have been prepared from adamantyl bromides and trimethylsilyl acetylenes. See Capozzi, G.; Ottana, R.; Giovanni, R.; Marcuzzi, F. *Gazz Chim. Ital.* 1985 115, 311 and Sasaki, T.; Usuki, A.; Ohno, M. *J. Org. Chem.* 1980 45 3559.

In the first step of our procedure for synthesizing 1,3-diethynyladamantane, adamantane is brominated in the presence of iron metal as a catalyst to yield 1,3-dibromoadamantane, in accordance with the following formula.

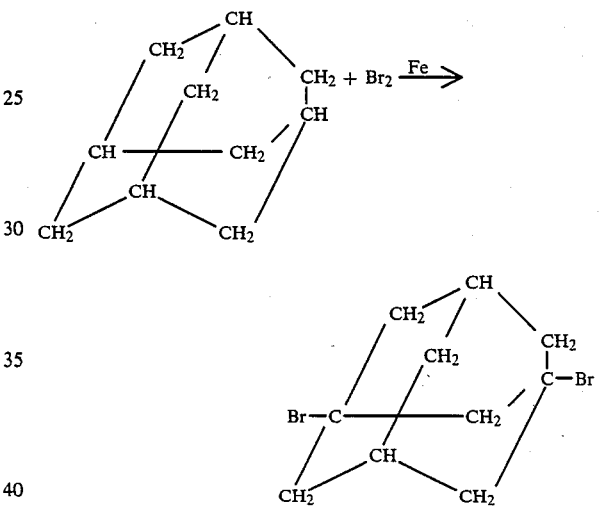

The reaction is carried out in excess bromine as a solvent and gives a high yield of 1,3-dibromoadamantane, typically in the order of 97%. Thus, the 1,3-dibromoadamantane product is sufficiently pure for use in subsequent steps of our procedure, but it can be made analytically pure by extraction with an equal volume of methanol and one recrystallization from the methanol. We make no claim to being the originators of this step, per se, since it has been reported in the literature (Likhotvorik, I. R.; Dovgan, N. L.; Danilenko, G. I. *Zh. Org. Khim.* 1977 13, 897). Next, the 1,3-dibromoadamantane is reacted with vinyl bromide in the presence of aluminum bromide as a catalyst to yield 1,3-bis(2,2-dibromoethyl)adamantane.

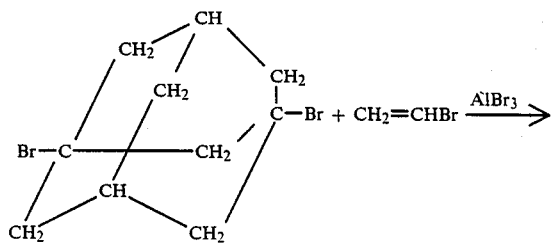

-continued

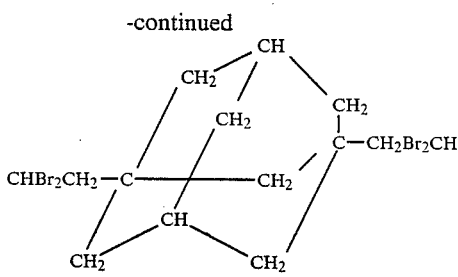

This reaction is a Friedel-Crafts alkylation of the vinyl bromide and is preferrably run at −20° C. in methylene chloride. We tried running the reaction in vinyl bromide solvent at −65° C., and found that great care in adding the aluminum bromide catalyst was required, to avoid an uncontrollable exotherm. When run in methylene chloride at −20° C., the exotherm was found to be much more controllable. Vinyl chloride can be used in place of the vinyl bromide in this step of our procedure and/or another Friedel-Crafts catalyst, such as ferric chloride, aluminum chloride or sulphuric acid, can be substituted for the aluminum bromide, but vinyl bromide and aluminum bromide are the respectively preferred reactant and catalyst for our purpose.

We have attempted, without success, to isolate the pure 1,3-bis(2,2-dibromoethyl)adamantane product of our Friedel-Crafts alkylation reaction. The material appears to dehydrohalogenate spontaneously to give mixtures containing moderate amounts of bromovinyl derivatives. This crude material could be converted directly to 1,3-diethynyladamantane, without any purification. The conversion of the 1,3-dibromoadamantane to 1,3-bis(2,2-dibromoethyl)adamantane can be easily monitored by thin layer chromatography.

The choice of dehydrohalogenation conditions for the 1,3-bis(2,2-dibromoethyl)adamantane product of the above reaction can vary, but we have experimentally determined that a preferred way of carrying out the dehydrohalogenation step is with potassium t-butoxide in 1-methyl-2-pyrrolidone at 170°–190° C. Other commonly used dehydrohalogenation reagents, such as, for example, potassium hydroxide and potassium t-butoxide in diethylene glycol yield 1,3-diethynyladamantane, but it can then be isolated only in low yields because it codistils with solvent from the resulting reaction mixture. When potassium t-butoxide in 1-methyl-2-pyrrolidone is employed within the above-indicated temperature range, the 1,3-diethynyladamantane is recovered from the reaction mixture and purified by distillation and recrystallization from ethanol. When so dehydrohalogenated, we found the isolated yield from adamantane to be 60 percent. This dehydrohalogenation step of our method is illustrated below.

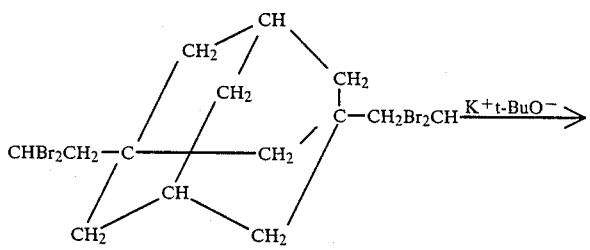 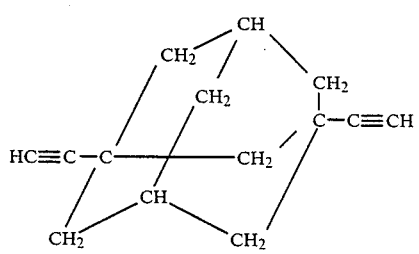

The literature reveals that adamantanes generally increase the glass points and hardness of polymer systems incorporating them. See Khardin, A. P.; Radchenko, S. S. *Russ. Chem. Rev.* 1982 51 272. To illustrate, polyadamantane prepared from dibromodiadamantane and sodium has a melting point greater than 420° C., and crystallinity greater than 80% on the basis of X-ray data (see Reinhardt, H. F. *J. Polym. Sci.*, B2, *Polym. Letters* 1964, 567). Even the introduction of small amounts of adamantane units into acrylate and similar polymer systems results in increased Tg (glass transition temperature). See again the Khardin et al. reference cited above.

The Stetter and Goebel reference, also cited above, discloses the synthesis of 1-ethynyladamantane from 1-bromoadamantane in good yield. We repeated that procedure with minor modifications by reacting 1-bromoadamantane with vinyl bromide in the presence of aluminum bromide to give the 2,2-dibromoethyl derivative, then dehydrobrominating that derivative in situ with potassium t-butoxide in triethylene glycol to give 1-ethynyladamantane in 60% overall yield.

We have determined experimentally that the thermal polymerization of 1,3-diethynyladamantane gave low molecular weight oligomers over a period of 12 to 80 hours at 230° C. and that heating at 290°–300° C. for 5–30 minutes was required for a fully cured polymer. The 1,3-diethynyladamantane monomer was observed to have high volatility, distilling readily at 80° C. at a pressure of 1 mm. of Hg and at about 240° C. at a pressure of 760 mm. of Hg. Because of this high volatility, the monomer cannot be polymerized in open vessels. It evaporates too easily at atmospheric pressure. This problem can be overcome by carrying out the polymerization in a sealed system, or by initially preparing nonvolatile oligomers, then curing them.

DESCRIPTION OF THE PREFERRED EMBODIMENTS

We have prepared polymers of 1,3-diethynyladamantane by heating the material under vacuum in sealed glass tubes. We found that when such tubes were placed directly in a preheated 290° C. furnace, a very brittle caramel-colored polymer was formed within one to five minutes. Stronger polymer samples, however, were obtained by placing the tubes of monomer in cold ovens and heating them to 290°–320° C. over several hours. Prolonged heating of the monomer in sealed tubes below 200° C. caused no change therein.

Our best results were obtained by heating the diacetylene in a sealed tube at 230° C. for sixteen hours and then raising the temperature to 290°–320° C. for thirty minutes. Rods of resin 5 millimeters in diameter and 20 millimeters long prepared in this manner were transparent and light brown in color and difficult to break with the fingers. Prolonged heating of these resins at 300° C. was found to have no apparent effect on the material.

We have found that the heating of samples of 1,3-diethynyladamantane at 230° C. produces oligomers in quantities dependent upon the heating time, as summarized in the table below.

| Heating Time in Hours | Percent of Monomer Recovered |
|---|---|
| 12.5 | 40 |
| 50 | 20 |
| 80 | 17 |

After the unreacted monomer is removed from the heated sample, the oligomer or prepolymer can be heated at 290° C. for 30 minutes to give cured specimens. The prepolymer prepared in a 12.5 hour heating period was found to have a melting point of 200°–230° C., and fused below the cure temperature to give a strong, rigid rod when cured in an open test tube. However, prepolymers prepared over a 50 hour, or longer, heating period failed to melt appreciably and gave brittle samples when cured.

Thermal stability data for the cured polymer was attained by TGA. The thermooxidative stability of the tested samples was found to be dependent on the method under which they were cured, but a sample that was cured in stages to 320° C. did not show significant weight loss to about 470° C.

Attempts to polymerize 1-ethynyladamantane revealed that it did not undergo polymerization under conditions that resulted in ready polymerization of the diethynyl compound. Heating of the monoacetylene to 270° C. produced no reaction and only starting material was recovered thereafter. Raising the heating temperature to 290° C. caused slow darkening of the 1-ethynyladamantane, but even after several days, most of the monomer was unreacted. Heating of the monoacetylene above 300° C. resulted in the formation of a tarry black material and evolution of a gas. The failure of 1-ethynyladamantane to polymerize was expected, and consistent with the behavior of other highly hindered acetylenes. But, by the same token, the reactivity of the diacetylene was unexpected.

Although 1-ethynyladamantane did not polymerize, that compound did, we discovered, copolymerize readily with 1,3-diethynyladamantane. Our work revealed that a 4:1 mixture of 1,3-diethynyladamantane and 1-ethynyladamantane produced a polymer when heated at 230° C. for 24 hours and thereafter cured at 290° C. for 30 minutes. The polymer was similar in color and strength to the homopolymer of 1,3-diethynyladamantane.

Following are examples included to specifically illustrate procedures generally described hereinabove. It is to be understood that these examples are offered merely as a means of illustration and are not intended to limit the scope of the invention to any particular combinations of materials, conditions, proportions, etc., set forth therein.

EXAMPLE I

Preparation of 1,3-dibromoadamantane

To a stirred mixture of 666 ml of bromine, 10 g of iron powder and a few drops of water at ambient temperature, was added, portionwise, 150 g (1.1 mol) of solid adamantane over a 2 h. period. Large amounts of hydrogen bromide gas were evolved. The mixture was stirred an additional 2 h., and then added cautiously over 1 h. to 5 l. of a 10% aqueous sodium bisulfite-ice mixture to which solid sodium bisulfite and ice were added as necessary to maintain the temperature below 50° C. and discharge the bromine color. Then the mixture was cooled and extracted with 1 l. and 2×500 ml of methylene chloride. The methylene chloride solution was dried (MgSO$_4$), treated with charcoal, filtered and evaporated to give 305 g of a crude pale brown solid: mp 105°–110° C. This product was extracted with 1 l. of methanol, filtered and dried to give 277 g (86%) of 1,3-dibromoadamantane: mp 110°–111° C.; TLC on silica wth hexane, R$_f$0.6; NMR δ3.0 (s, 2H), 2.5 (s, 10H), 1.95 (s, 2H) ppm. EXAMPLE II Preparation of 1,3-bis(2,2-dibromoethyl)adamantane A solution of 147 g (0.5 mol) of 1,3-dibromoadamantane and 300 ml (3 mol) of vinyl bromide in 250 ml of methylene chloride was stirred and cooled to −20° C. in an ice-methanol bath and then 25 g (0.094 mol) of aluminum bromide was added portionwise over 1 h. The mixture was stirred for 2 h. during which time the temperature was allowed to rise to ambient. The solution was washed with 100 ml of water, 250 ml of concentrated aqueous hydrochloric acid, and 100 ml of water, dried (MgSO$_4$) and evaporated to give 292 g of an oil. This material contained 1,3-bis(2,2-dibromoethyl)adamantane and polyvinyl bromide, and was used without further purification.

EXAMPLE III

Preparation of 1,3-diethynyladamantane

A mixture of 292 of crude 1,3-bis(2,2-dibromoethyl)adamantane [prepared from 147 g (0.5 mol) of 1,3-dibromoadamantane] and 300 g (3.6 mol) of potassium t-butoxide in 1 l. of 1-methyl 2-pyrrolidone was heated to 180° C. and the distillate, bp 85° C., (identified as t-butanol by NMR) was collected. After 135 ml (1.2 mol) of t-butanol was collected (3 h.), no further distillate was formed and the mixture was cooled, diluted with 2 l. of water and extracted with 3×500 ml of hexane. The combined hexane extracts were washed with 500 ml of water, dried (MgSO$_4$) and evaporated to give 93 g of a clear oil. The crude oil was purified by bulb to bulb distillation to give 63.4 g (70% based 1,3-dibromoadamantane) of 1,3-diethynyladamantane: mp 46° C. (ethanol); bp 80°–82° C. (1.0 mm); IR 3250 (acetylene C—H), 2950 (C—H), 2150 (acetylene C—C) cm$^{-1}$; NMR δ1.4–2.0 (m) ppm.

Anal. Calcd for C$_{14}$H$_{16}$: C, 91.16; H, 8.75. Found: C, 90.96; H, 8.87.

EXAMPLE IV

Preparation of poly-1,3-diethynyladamantane

In a 5 mm×8 mm glass tube was placed 0.5 g of melted (50° C.) 1,3-diethynyladamantane, and the tube was cooled to −65° C., evacuated, and sealed. The tube was heated at 230° C. for 16 h. and then 290° C. for 30 min. The tube was cooled and opened (no pressure was noted) to give a transparent, light brown rod.

EXAMPLE V

Preparation of poly-1,3-diethynyladamantane prepolymer

A 1.0 g sample of 1,3-diethynyladamantane was sealed in a tube as described for the homopolymerization and heated at 230° C. for 12.5 h. The tube was cooled and opened, and the unreacted monomer removed by heating above 150° C. in vacuo for 10–15 min. The residual waxy solid (1.6 g, 60%) was soluble in acetone and melted at 200°–230° C.; molecular weight (VPO, acetone) 442.

The next example describes the preparation of 1-ethynyladamantane somewhat along lines set forth in the Stetter and Goebel reference cited heretofore. We do not claim originality of this procedure, and include it here only to illustrate the manner in which we obtained starting material for use in the polymerization procedure of EXAMPLE VII to follow.

EXAMPLE VI

Preparation of 1-ethynyladamantane

A solution of 45 g (0.17 mol) of 1-bromoadamantane in 60 ml of vinyl bromide was cooled to −65° C. and 10 g of aluminum bromide was added portionwise over 2 h. The mixture was then poured on to 500 g of ice, neutralized with 10% aqueous sodium carbonate solution, and extracted with 3×100 ml of methylene chloride. The combined extracts were dried (MgSO$_4$) and evaporated to yield 70 g of an oil containing 1-(2,2-dibromoethyl)adamantane and polyvinyl bromide (NMR). This oil was dissolved in 100 ml of triglyme, 38 g (0.34 mol) of potassium t-butoxide added, and the mixture heated at 160° C. for 3 h. The mixture was cooled, diluted with 300 ml of water and extracted with 3×100 ml of hexane. The combined hexane extracts were dried (MgSO$_4$), and distilled to give 12 g (52% based on 1-bromoadamantane) of 1-ethynyladamantane: mp 82°–83° C.; bp 95–100 (1 mm); NMR δ1.9–2.6 ppm.

EXAMPLE VII

Preparation of copolymer of 1-ethynyladamantane and 1,3-diethynyladamantane

A mixture of 0.05 g of 1-ethynyladamantane and 0.20 g of 1,3-diethynyladamantane was heated in a sealed tube at 230° C. After 24 h., the mixture, which contained some liquid, was heated at 290° C. for 30 min. The tube was cooled, opened and the transparent light brown colored rod (0.25 g) was removed. When this resin was heated at 150° C. (1.0 mm) for 15 min., no weight loss occurred, indicating that no acetylene monomers remained.

As will now be apparent, the scope of the present invention encompasses a new diacetylene compound, a method of preparing that compound and methods of polymerizing it with itself and with a monoacetylene counterpart thereof. The following claims are intended to encompass this diverse subject matter and it should be noted that the reach of the invention extends to all the variant forms thereof within the scope of the claim language. So that there will be no misunderstanding as to their import, the terms "polymerizing" and "polymerized product" set forth in the claims are intended to encompass both prepolymer and cured polymer concepts.

We claim:

1. A method of polymerizing ethynyl-substituted adamantane monomers selected from the group consisting of 1,3-diethynyladamantane monomers and mixtures of 1-ethynyladamantane and 1,3-diethynyladamantane monomers which comprises heating the monomers under suitable temperature and time conditions for the purpose.

2. A method in accordance with claim 1 in which the ethynyl-substituted monomers are 1,3-diethynyladamantane monomers.

3. A method in accordance with claim 2 in which the heating of the monomers under suitable temperature and time conditions comprises heating said monomers at about 230° C. for a period of from about 12 hours to about 80 hours.

4. A method in accordance with claim 3 in which the heating of said monomers at about 230° C. is followed by additional heating thereof at from about 290° to about 320° C. for from about 5 to about 30 minutes.

5. A method in accordance with claim 4 in which the 230° C. heating period is about 16 hours and the from about 290° to about 320° C. heating period is about 30 minutes.

6. A method in accordance with claim 5 in which the heating temperature of from about 290° to about 320° C. is about 290° C.

7. A method in accordance with claim 2 in which the heating of the monomers under suitable temperature and time conditions comprises heating said monomers to from about 290° to about 320° C. and maintaining them thereat for a suitable time period.

8. A method in accordance with claim 3 in which the period of from about 12 hours to about 80 hours is 12.5 hours, and which includes a follow-up heat treatment at about 290° C. under atmospheric pressure for curing purposes.

9. A method in accordance with claim 1 in which the ethynyl-substituted monomer are made up of a mixture of 1-ethynyladamantane and 1,3-diethynyladamantane monomers.

10. A method in accordance with claim 9 in which the weight ratio of 1-ethynladamantane monomers to 1,3-diethynyladamantane monomers in said mixture is 1:4.

11. A method in accordance with claim 10 in which the heating of the monomers under suitable temperature and time conditions comprises heating said monomers at about 230° C. for about 24 hours and thereafter at about 290° C. for about 30 minutes.

12. A polymerized product formed from monomers selected from the group consisting of 1,3-diethynyladamantane monomers and mixtures of 1-ethynyladamantane and 1,3-diethynyladamantane monomers.

13. A polymerized product in accordance with claim 12 formed from 1,3-diethynyladamantane monomers.

14. A polymerized product in accordance with claim 12 formed from a mixture of 1-ethynyladamantane and 1,3-diethynyladamantane monomers.

* * * * *